US010954551B2

(12) United States Patent
Glezer

(10) Patent No.: US 10,954,551 B2
(45) Date of Patent: Mar. 23, 2021

(54) DEVICES, SYSTEMS, AND METHODS FOR SINGLE MOLECULE, REAL-TIME NUCLEIC ACID SEQUENCING

(71) Applicant: Singular Genomics Systems, Inc., San Diego, CA (US)

(72) Inventor: Eli Glezer, Del Mar, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 211 days.

(21) Appl. No.: 15/914,835

(22) Filed: Mar. 7, 2018

(65) Prior Publication Data

US 2018/0258472 A1 Sep. 13, 2018

Related U.S. Application Data

(60) Provisional application No. 62/468,828, filed on Mar. 8, 2017.

(51) Int. Cl.
*C12Q 1/68* (2018.01)
*C12Q 1/6818* (2018.01)
*C12Q 1/6874* (2018.01)
*G01N 21/64* (2006.01)

(52) U.S. Cl.
CPC ......... *C12Q 1/6818* (2013.01); *C12Q 1/6874* (2013.01); *G01N 21/6428* (2013.01); *G01N 21/6456* (2013.01); *C12Q 2535/122* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 8,911,972 B2 * | 12/2014 | Chaisson | C12Q 1/6869 435/91.2 |
| 8,927,212 B2 | 1/2015 | Kong et al. | |
| 9,353,412 B2 | 5/2016 | He et al. | |
| 9,862,998 B2 | 1/2018 | He et al. | |
| 10,077,475 B2 | 9/2018 | Kartalov et al. | |
| 10,233,493 B2 | 3/2019 | He et al. | |
| 2019/0194721 A1 | 6/2019 | Xi et al. | |
| 2019/0376136 A1 | 12/2019 | He et al. | |

OTHER PUBLICATIONS

Fuller et al. (PNAS, 2016, 113(19)5233-5238) (Year: 2016).*
Berezhna S.Y et al. (Jul. 11, 2012, e-published Jun. 29, 2012). "Single-molecule Förster resonance energy transfer reveals an innate fidelity checkpoint in DNA polymerase I," Journal of the American Chemical Society 134(27):11261-11268.
Corry B. et al. (Dec. 2005, Sep. 30, 2005). "A Flexible Approach to the Calculation of Resonance Energy Transfer Efficiency between Multiple Donors and Acceptors in Complex Geometries," Biophysical Journal 89:3822-3836.
Eid J. et al. (Jan. 2, 2009, e-published Nov. 20, 2008). "Real-time DNA sequencing from single polymerase molecules," Science 323(5910):133-138.
Evans G.W. et al. (Jul. 13, 2015, e-published May 26, 2015). "Real-time single-molecule studies of the motions of DNA polymerase fingers illuminate DNA synthesis mechanisms," Nucleic Acids Res. 43(12):5998-6008.
Fairhead M. et al. (2015). "Site-specific biotinylation of purified proteins using BirA," Methods in Molecular Biology 1266:171-184.
Fuller C.W. et al. (May 10, 2016, e-published Apr. 18, 2016). "Real-time single-molecule electronic DNA sequencing by synthesis using polymer-tagged nucleotides on a nanopore array," PNAS USA 113(19):5233-5238.
Gupta P.K. (Nov. 2008, e-published Aug. 21, 2008). "Single-molecule DNA sequencing technologies for future genomics research," Trends Biotechnol. 26(11):602-611.
Joyce C.M et al. (Jun. 2008, e-published May 13, 2008). "Fingers-closing and other rapid conformational changes in DNA polymerase I (Klenow fragment) and their role in nucleotide selectivity," Biochemistry. 47(23):6103-6116.
Kunkel T.A. (Apr. 23, 2004, e-published Feb. 26, 2004). "DNA replication fidelity," The Journal of Biological Chemistry. 279(17):16895-16898.
Lakowicz J.R et al. (1988). "Principles of frequency-domain fluorescence spectroscopy and applications to cell membranes," Subcell Biochem. 13:89-126.
Li Y. et al. (Dec. 15, 1998). "Crystal structures of open and closed forms of binary and ternary complexes of the large fragment of Thermus aquaticus DNA polymerase I: structural basis for nucleotide incorporation," The EMBO Journal. 17(24):7514-7525.
Maliwal B.P. et al. (Jan. 17, 2012). "Extending Förster resonance energy transfer measurements beyond 100 A using common organic fluorophores: enhanced transfer in the presence of multiple acceptors," J Biomed Opt. 17(1):011006.
Miller N.A. et al. (Sep. 2015). "A 26-hour system of highly sensitive whole genome sequencing for emergency management of genetic diseases," Genome Med. 7:100.
Osheroff W.P. et al. (Feb. 1999). "The fidelity of DNA polymerase beta during distributive and processive DNA synthesis," The Journal of Biological Chemistry. 274(6):3642-3650.
Ossola A. (Sep. 30, 2015). Your Full Genome Can Be Sequenced for Just $1000. Popular Science, 7 pages.
Pomerantz R.T. et al. (Apr. 2007, e-published Mar. 9, 2007). "Replisome mechanics: insights into a twin DNA polymerase machine," Trends Microbiol. 15(4):156-164.
Rodriguez A.C. et al. (Jun. 2, 2000). "Crystal structure of a pol alpha family DNA polymerase from the hyperthermophilic archaeon *Thermococcus* sp. 9 degrees N-7," Journal of Molecular Biology 299(2):447-462.

(Continued)

*Primary Examiner* — Stephanie K Mummert
(74) *Attorney, Agent, or Firm* — Mintz Levin Cohn Ferris Glovsky and Popeo P.C.

(57) ABSTRACT

Methods, systems, and reagents for real-time single molecule sequencing of nucleic acids, particularly long DNA molecules, is described. Preferably, such methods and systems combine FRET (Förster Resonance Energy Transfer)-based proximity sensing of labeled nucleotides in or near a DNA polymerase's active site with FRET-based monitoring of the conformational changes in the polymerase that occur during nucleotide incorporation.

10 Claims, 5 Drawing Sheets

(56) References Cited

OTHER PUBLICATIONS

Santoso Y. et al. (Jan. 12, 2010, e-published Dec. 18, 2009). "Conformational transitions in DNA polymerase I revealed by single-molecule FRET," PNAS USA 107(2):715-720.
Schirmer M. et al. (Mar. 31, 2015, e-published Jan. 13, 2015). "Insight into biases and sequencing errors for amplicon sequencing with the Illumina MiSeq platform," Nucleic Acids Res. 43(6):e37.
Schneckenburger H. (Feb. 2005). "Total internal reflection fluorescence microscopy: technical innovations and novel applications," Curr Opin Biotechnol. 6(1):13-18.
Stengel G. et al. (Oct. 30, 2007, e-published Oct. 4, 2007). "Conformational dynamics of DNA polymerase probed with a novel fluorescent DNA base analogue," Biochemistry 46(43):12289-12297.

\* cited by examiner

DEVICES, SYSTEMS, AND METHODS FOR SINGLE MOLECULE, REAL-TIME NUCLEIC ACID SEQUENCING

CROSS REFERENCE TO RELATED APPLICATIONS

The present application claims priority to U.S. Provisional Application No. 62/468,828, filed Mar. 8, 2017, the disclosure of which is hereby incorporated by reference in its entirety.

STATEMENT REGARDING FEDERALLY SPONSORED RESEARCH OR DEVELOPMENT

Not Applicable.

BACKGROUND OF THE INVENTION

1. Field of the Invention

The present invention generally relates to nucleic acid sequencing, particularly to improved devices, systems, and methods for single molecule DNA and RNA sequencing with real-time error-checking to generate more accurate data.

2. Background

Nucleic acid sequencing is fundamental technology in life sciences. Sequencing of deoxyribonucleic acid (DNA) and ribonucleic acid (RNA) is used, for example, in scientific research, drug discovery, medical diagnostics, and, more recently, in the prevention, monitoring, and treatment of disease. The rapidly increasing use of DNA and RNA sequencing in such fields has increased demand for low-cost, extremely high throughput, accurate nucleic acid sequencing methods (Next Generation Sequencing, or "NGS", methods), systems, and reagents.

Despite significant reductions in cost and increases in speed of nucleic acid sequencing technologies, there are still challenges in obtaining long, accurate reads in a timely, cost effective manner. Short-read sequencing-by-synthesis (SBS) platforms, such as Illumina's and Thermo-Fisher's, have become the dominant sequencing technologies, but suffer from limitations in detecting structural variants, sequencing certain regions of the genome, amplification bias, long time to results (days) due to long cycle times, and extensive sample preparation requirements. To address some of these shortcomings, there has been considerable progress towards long-read real-time single-molecule sequencing (SMS) methods by companies including Pacific Biosystems and Oxford Nanopore. Among the proposed advantages of SMS vs. 2nd generation SBS are 1) increased read length; 2) potential for lower error rates due to simplified sample preparation; and 3) shorter cycle times (1). However, the error rates for current SMS methods is much greater than for short-read, amplified techniques. Additionally, the cost per gigabase (Gb) of DNA sequence is 10-100× greater, due to the lower throughput of current SMS systems.

Due to the tremendous potential to improve the speed, accuracy, and economy of DNA sequencing, a number of approaches to SMS have emerged. So far, the most successful commercial endeavor has been Pacific Biosciences single-molecule real-time (SMRT) approach, which reportedly can achieve about 85% single read base accuracy and read lengths approaching 15 kb (1). Other single molecule technologies include pore-based technologies that sense the presence of a nucleotide by reading a change in impedance or current as the DNA is passed through the pore (Oxford Nanopore and Genia) (5). Although these and other approaches support longer reads and reduction of artifacts due to sample preparation, reduction in error rates would lower the need for repeated reads and reduce sequencing time.

An ideal solution would enable the faster reads provided by the SMS approach, with the reduced error rates and higher throughput of the SBS platforms.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

The term "analogue", in reference to a chemical compound, refers to compound having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., and extension product) by a suitable polymerase, for example, a DNA polymerase in the context of a dNTP analogue.

The term "chromophore" refers to an atom or group whose presence is responsible for the color of a compound.

The term "combinatorial fluorescence energy transfer" or, more generally, "fluorescence energy transfer" refers to optical interactions that persist between two chromophores even when they are as far as 80 angstroms apart. The chromophore with high energy absorption is defined as a donor, and the chromophore with lower energy absorption is defined as an acceptor. Fluorescence energy transfer is mediated by a dipole-dipole coupling between the chromophores that results in resonance transfer of excitation energy from an excited donor molecule to an acceptor. See, e.g., published U.S. patent application publication no. 20060057565.

The term "complexity", in reference to a population of molecules, e.g., polynucleotides, means that a number of different species of the molecule (e.g., polynucleotides having different nucleotide sequences, sizes, etc.) are present in the population.

The term "complement" refers to a nucleic acid molecule or nucleotide that is complementary to the nucleotide, or nucleotide sequence, of another nucleic acid molecule.

The term "dye" refers to a chemical label that can be added to another substance to add a color that can be detected. Examples of dyes include fluorescent dyes, including FAM, Bodipy, TAMRA, and Alexa dyes.

"DNA" refers to deoxyribonucleic acid, a polymer of deoxyribonucleotides (e.g., dATP, dCTP, dGTP, dTTP, dUTP, etc.) linked by phosphodiester bonds. DNA can be single-stranded (ssDNA) or double-stranded (dsDNA), and can include both single and double-stranded (or "duplex") regions. "RNA" refers to ribonucleic acid, a polymer of ribonucleotides linked by phosphodiester bonds. RNA can be single-stranded (ssRNA) or double-stranded (dsRNA), and can include both single and double-stranded (or "duplex") regions. Single-stranded DNA (or regions thereof)

and ssRNA can, if sufficiently complementary, hybridize to form double-stranded complexes (or regions).

The term "DNA template" refers to any DNA molecule that may be bound by a DNA polymerase and utilized as a template for nucleic acid synthesis.

The term "dATP analogue" refers to an analogue of deoxyadenosine triphosphate (dATP) that is a substrate for a DNA polymerase.

The term "dCTP analogue" refers to an analogue of deoxycytidine triphosphate (dCTP) that is a substrate for a DNA polymerase.

The term "dGTP analogue" refers to an analogue of deoxyguanosine triphosphate (dGTP) that is a substrate for a DNA polymerase.

The term "dNTP analogue" refers to an analogue of deoxynucleoside triphosphate (dNTP) that is a substrate for a DNA polymerase The term "dTTP analogue" refers to an analogue of deoxythymidine triphosphate (dUTP) that is a substrate for a DNA polymerase.

The term "dUTP analogue" refers to an analogue of deoxyuridine triphosphate (dUTP) that is a substrate for a DNA polymerase.

The term "extendible" means, in the context of a nucleotide, primer, or extension product, that the 3'-OH group of the particular molecule is available and accessible to a DNA polymerase for addition of a dNTP or dNTP analogue.

The term "fluorophore" means a fluorescent chemical compound that can re-emit light upon light excitation. Fluorophores include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, Alexa dyes, phycoerythin, Bodipy, and others known in the art, see, e.g., Haugland, Molecular Probes Handbook (Eugene, Oreg.), 6th Edition; The Synthegen catalog (Houston, Tex.); Lakowicz, Principles of Fluorescence Spectroscopy, 2nd Ed., Plenum Press New York (1999), and WO 98/59066.

The term "identical", in the context of, for example, a particular set of "template DNA molecules" (e.g., the DNA molecules in a particular "cluster" on an NGS flow cell), will mean that all such molecules have the same nucleotide sequence.

The term "independently resolvable" means that the entity under study can be examined independent of other entities due to spatial separation, for example, one polymerase-template complex can be probed independent from another polymerase-template complex present at a different physical location, or "address", on the solid substrate.

The terms "iterating" and the like mean to repeat.

The term "label" refers to one or more atoms that can be specifically detected to indicate the presence of a substance to which the one or more atoms is attached. A label can be a primary label that is directly detectable or secondary label that can be indirectly detected, for example, via direct or indirect interaction with a primary. Labels include dyes, chromophores, combinatorial fluorescence energy transfer labels, electrophores, fluorsophores, mass labels, and radiolabels.

The term "mass label" means a molecular entity of a known or predetermined mass that is capable of being covalently attached, preferably via by a cleavable bond, to another chemical compound, e.g., a protein, nucleotide, etc.

The terms "measure", "measuring", "measurement" and the like refer not only to quantitative measurement of a particular variable, but also to qualitative and semi-quantitative measurements. Accordingly, "measurement" also includes detection, meaning that merely detecting a change, without quantification, constitutes measurement.

The term "nucleotide" is defined herein to include both nucleotides and nucleosides, including deoxynucleotides, ribonucleotides, and analogues thereof. Nucleosides, as for nucleotides, comprise a purine or pyrimidine base linked glycosidically to ribose or deoxyribose, but they lack the phosphate residues that would make them a nucleotide. Synthetic and naturally occurring nucleotides are included within the definition, as are those that are labeled and/or blocked. The term "nucleoside" includes natural nucleosides, including 2'-deoxy and 2'-hydroxyl forms, e.g. as described in Kornberg and Baker, DNA Replication, $2^{nd}$ Ed. (Freeman, San Francisco, 1992), as well as non-naturally occurring forms, for example, a 7-deazapurine base, a pyrazole[3,4-d]pyrimidine base, a propynyl-dN base, or other analogues or derivatives known in the art. "Analogues" in reference to nucleosides include synthetic nucleosides having modified base moieties and/or modified sugar moieties, see, e.g., Scheit, Nucleotide Analogues (John Wiley, New York, 1980); Uhlman and Peyman, Chemical Reviews, 90:543-584 (1990), or the like, with the only proviso that they are capable of specific hybridization to a complementary base in another DNA molecule. Such analogues include synthetic nucleosides designed to enhance binding properties, reduce complexity, increase specificity, and the like.

A "patentable" process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

The term "population" refers to a collection of one or more entities, e.g., DNA molecules.

"Perfectly matched" in reference to a nucleic acid duplex means that the poly- or oligonucleotide strands making up the duplex form a double-stranded structure, or region of double-stranded structure, with one another such that every nucleotide (or nucleotide analogue) in each strand undergoes Watson-Crick base-pairing with a nucleotide in the other strand in the duplexed (i.e., hybridized) region. The term also comprehends the pairing of nucleoside analogues, such as deoxyinosine, nucleosides with 2-aminopurine bases, and the like. Conversely, a "mismatch" in a nucleic acid duplex means that one or more pairs of nucleotides in the duplex fail to undergo Watson-Crick base-pairing.

A "polymerase-template complex" refers to functional complex between a DNA polymerase and a DNA template molecule being sequenced.

The term "radiolabel" refers to an isotopic label such as a naturally non-abundant radioactive or heavy isotope, including but not limited to $^{14}C$, $^{123}I$, $^{124}I$, $^{125}I$, $^{131}I$, $^{32}P$, $^{35}S$, and $^{3}H$.

A "removable" group, e.g., a label or a blocking group, refers to a chemical group that can be removed from a dNTP analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that all of the removable group be removed, only that a sufficient portion of it be removed such that a DNA polymerase can extend a nucleic acid by incorporation of at least one additional nucleotide or dNTP analogue.

The terms "sequencing", "sequence determination", "determining a nucleotide sequence", and the like include determination of partial as well as full sequence information of the polynucleotide being sequenced. That is, the term includes sequence comparisons, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide.

The term "sequencing reaction mixture" refers to an aqueous mixture that contains the reagents necessary to allow a dNTP or dNTP analogue to be incorporated into a DNA strand by a DNA polymerase.

The term "solid substrate" means any suitable medium present in the solid phase to which an antibody or an agent can be covalently or non-covalently affixed or immobilized. Preferred solid substrates are glass.

The term "species", when used in the context of describing a particular compound or molecule species, refers to a population of chemically indistinct molecules.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

As used herein, the singular forms "a", "an", and "the" include plural references unless the context clearly dictates otherwise.

As used herein, the term "about" refers to approximately a +/−10% variation from the stated value. It is to be understood that such a variation is always included in any given value provided herein, whether or not it is specifically referred to.

SUMMARY OF THE INVENTION

The present invention concerns DNA/RNA sequencing methods and systems that provide long reads with high accuracy and high throughput, with the following benefits: 1) simplification and reduced cost of sample preparation; 2) elimination of errors produced by clonal amplification of sample DNA or RNA; 3) the ability to assess large structural variations in human genes or genes associated with different pathogenic strains of viruses or bacteria; 4) the potential to enable rapid clinical diagnoses; 5) the ability to read homopolymeric sequences; and 6) the ability to sequence highly methylated regions of the genome (4-6). Here, to significantly improve the accuracy of real-time SMS, FRET (Förster Resonance Energy Transfer)-based proximity sensing of labeled nucleotides near the polymerase is combined with FRET-based monitoring of the conformational changes in the polymerase that occur during nucleotide incorporation. Detecting the polymerase's conformational change serves to verify that the polymerase has in fact incorporated the particular labeled nucleotide analogue detected, rather than just transiently binding the nucleotide analogue, thus greatly reducing the rate of insertion errors due to false detection. Additionally, by reducing the chance of false detection, the conformational readout allows the threshold for proximity detection to be lowered, thus also reducing deletion errors (due to rapid nucleotide incorporation that could otherwise be missed).

Reagent kits and systems for performing such methods are related aspects of the invention.

The foregoing and other objects, features, and advantages of the invention will be apparent from the following more particular descriptions of preferred embodiments of the invention as illustrated in the accompanying drawings.

BRIEF DESCRIPTION OF THE DRAWINGS

This document contains at least one drawing executed in color. Copies of this patent or patent application publication with color drawing(s) will be provided by the Office upon request and payment of the necessary fee.

In the second example (FIG. 1, part B), a cascading FRET approach is shown, using a combination proximity detection of nucleotides with the conformational state monitoring of the polymerase. The illustration on the left shows the polymerase (blue) in its open conformation bound to the template. On the right, the polymerase is shown in its closed conformation (green), with the A1-labeled-dNTP being incorporation into the daughter strand. A Donor moiety (D) is positioned on the "thumb" region of the polymerase, and the Intermediate acceptor/donor moiety (Int.) on the polymerase's "fingers". The final Acceptors (4 different dye complexes) in these embodiments are attached to the terminal phosphates on each of the nucleotide analogues (A1, A2, A3, and A4). When the complementary next nucleotide to be added to the primer extension product associates with the template strand in the polymerase's active site and the polymerase is in the "closed" position, there will be a cascading energy transfer process, from the optically excited Donor, to the Intermediate (acceptor/donor), and then on to the final Acceptor. The process iterates for each labeled-dNTP added by the polymerase. In some embodiments, the cascade process involves an energy transfer through one or more Donor moieties, one or more Intermediate moieties (Int), and one or more Acceptor moieties (A). In some embodiments, the "Donors" and "Acceptors" are multi-dye complexes, to enhance the magnitude of the FRET signal.

In other examples of FRET-based nucleotide proximity and conformational sensing, a first FRET Donor (D) moiety, or multiple donor and/or intermediate moieties forming a first donor complex, and a first Acceptor moiety, or multiple acceptor and/or intermediate moieties forming a first acceptor complex, is used to detect the conformational state of the polymerase. For example, a Donor moiety (D) is positioned on the "fingers" region of the polymerase, and an Acceptor moiety (A0) is positioned on the "thumb" region; alternatively, a Donor moiety (D) is positioned on the "thumb" region of the polymerase, and an Acceptor moiety (A0) is positioned on the "fingers" region. Energy transfer can occur between the first donor and first acceptor when the polymerase transitions from an "open" to a "closed" conformation. Similarly, nucleotide proximity sensing can be accomplished using a set of second donors and second acceptors. Here, the second donor and acceptor moieties (or complexes) are positioned such that energy transfer between them can occur when the complementary next labeled nucleotide analogue to be added to the primer extension product associates with the template strand in the polymerase's active site but does not occur between the first donor and a second acceptor moiety.

Figure 2:
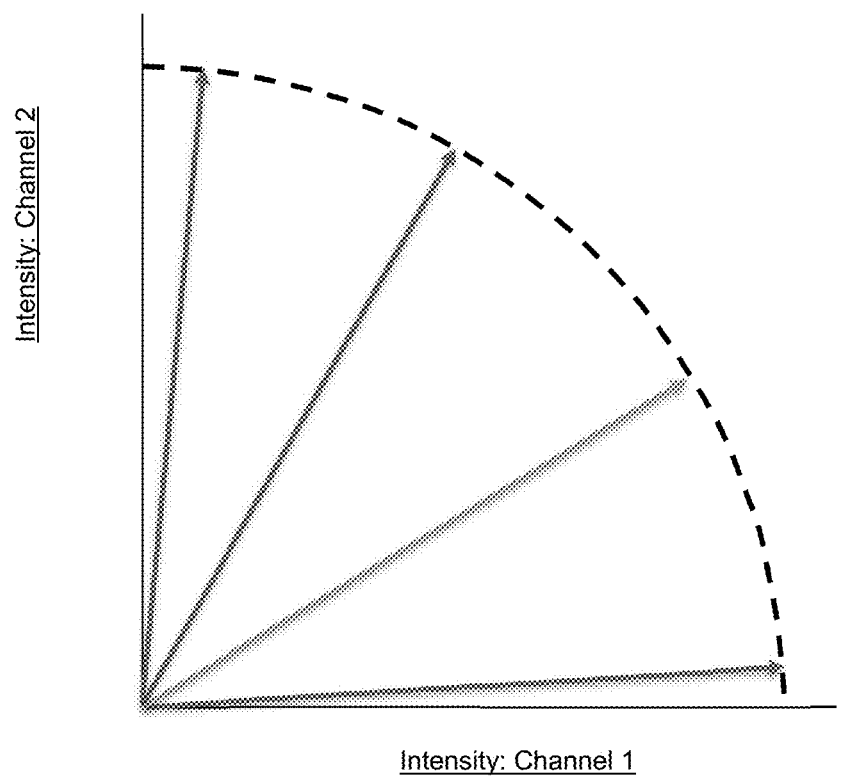

FIG. 2 shows an example of how 4 fluorescent signals can be resolved in 2 spectral channels.

Figure 3:
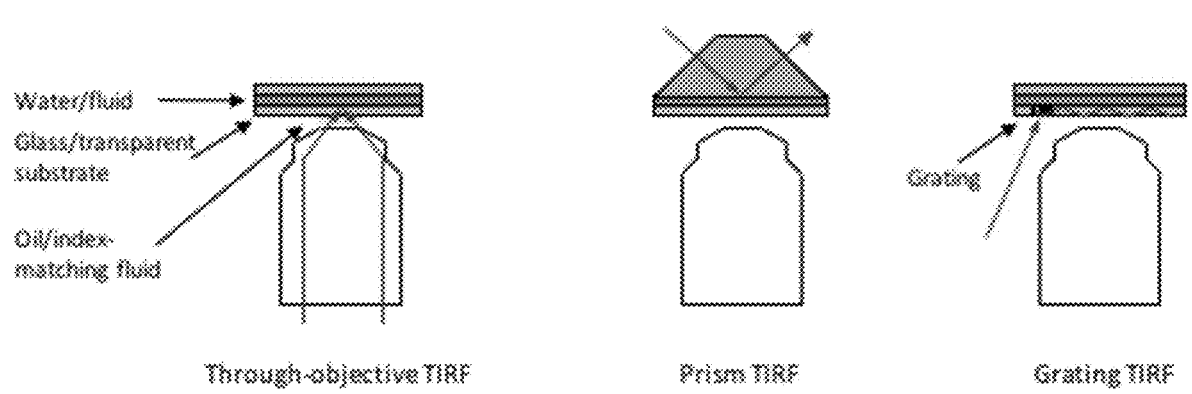

FIG. 3 shows three examples of optical configurations for Total Internal Reflection Fluorescence (TIRF) measurements: 1) through-objective TIRF; 2) Prism-coupled TIRF; and 3) Grating-coupled TIRF. In each of the three configurations, the light is delivered at an angle greater than the critical angle of the glass/water interface. Another possible configuration (not shown) is transverse coupling into the transparent substrate or waveguide.

Figure 4:
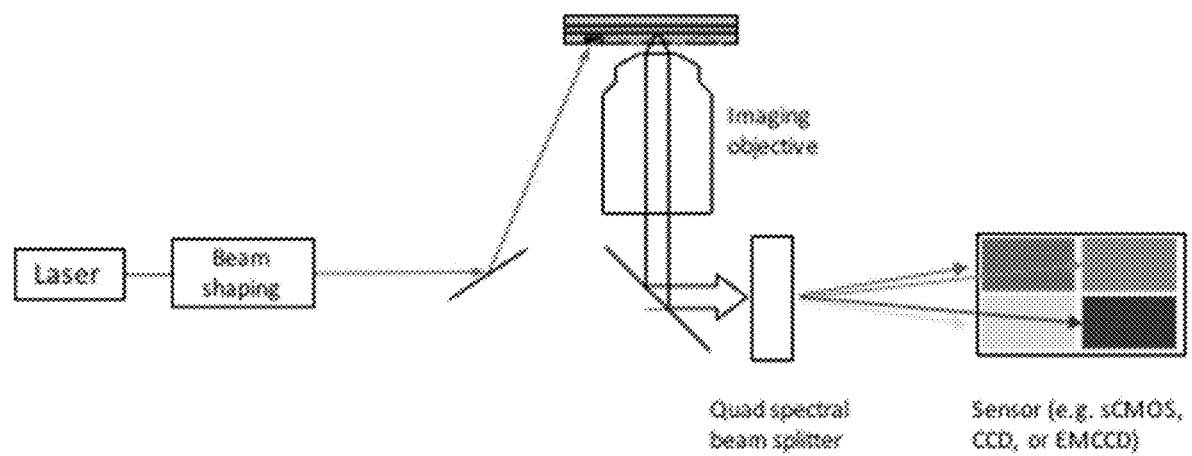

FIG. 4 shows an example schematic of the optical system for TIRF microscopy, with readout of 4 spectral channels for simultaneous detection of multiple FRET signals.

Figure 5:
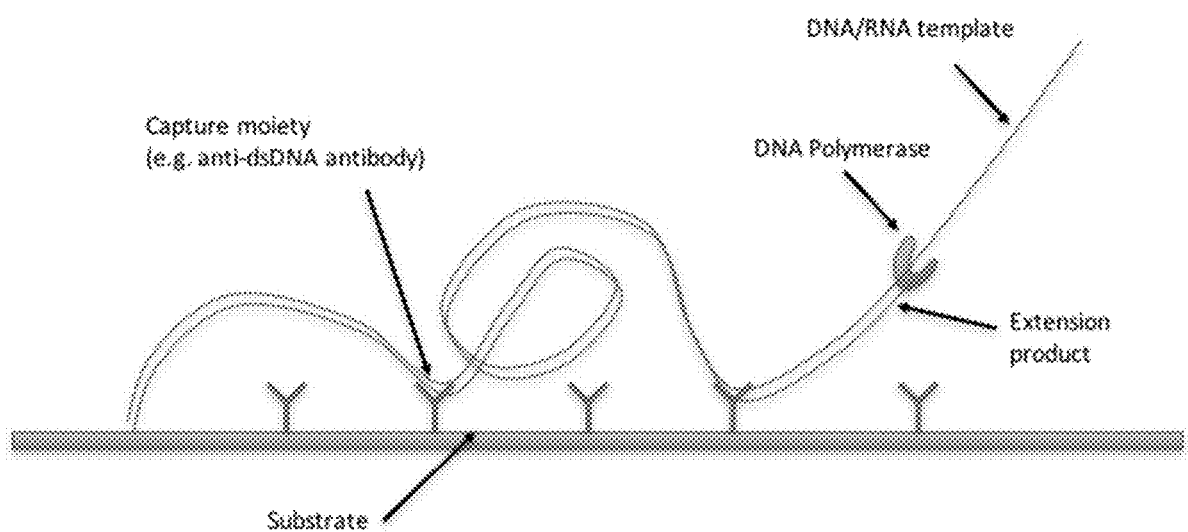

FIG. 5 shows a DNA template in the process of being extended. As the double-stranded DNA is formed, it becomes tethered to the surface at additional attachment points, via binding to capture molecules, such as antibodies that bind dsDNA.

The foregoing and other aspects of the invention will become more apparent from the following detailed description and the claims. Unless otherwise defined in this specification, all technical and scientific terms used herein have the same meaning as commonly understood by one of ordinary skill in the art to which this invention pertains.

DETAILED DESCRIPTION

Currently available DNA sequencing technology has permitted the rapid and relatively economical acquisition of data that has driven the widespread adoption of this valuable research and diagnostic tool. Indeed, since the announcement in 2000 of the first sequencing of the human genome, the cost of sequencing the human genome has dropped from $2.7 billion from to about $1,000 (2). In the same time interval, the required time to sequence a human genome has decreased from 10 years to about 26 hours (3). Despite these substantial improvements, there remains significant unmet need to improve the speed and accuracy of DNA sequencing to increase the availability of high quality data and to permit a wider adoption of sequencing as a diagnostic technology. Current technologies that permit high-throughput sequencing include "2nd generation" include sequencing by synthesis (SBS) technologies from Illumina and Thermo-Fisher. These technologies have many drawbacks, including: 1) a higher single read error rates compared to first generation Sanger sequencing; 2) shorter read lengths (compared to first generation sequencing); 3) complex sample preparation; 4) artifacts/errors produced by the clonal amplification of templates that are required to produce an adequate signal; and 5) long cycle times (5-30 minutes), which prevent the generation of rapid sequencing results (3).

To address these drawbacks, this invention provides sequencing devices, systems, and methods that monitor and sense the proximity of labeled nucleotide analogues as well as the conformation of the DNA polymerase, which polymerase maintains enzymatic activity when labeled with one or more energy donor moieties (FIG. 1, D) in its "thumb" region and one more intermediate energy transfer moieties (FIG. 1, Int) in its "fingers" region to permit reliable single molecule FRET (smFRET) detection of polymerase motion. Nucleotide analogues are labeled with acceptor complexes (FIG. 1, A1-A4) that provide a strong FRET signal, and the polymerase preferably has a nucleotide incorporation rate, or "processivity", on the order of about 1-1,000 based per second, with a processivity of about 5-10 bases/sec. being particularly preferred. In some embodiments, the longer reads (>300 bases) are generated by automatic on/off replacement of the polymerase. In preferred embodiments, the combination of proximity and conformational readouts improves accuracy relative to other single-molecule sequencing methods, such that accuracies exceed about 90%, 95%, or even 99% or more with read lengths of 300-1,000,000 bases or more. Preferred devices have optimized optical configurations for total internal reflection fluorescence (TIRE) excitation coupling (prism or grating based), and a detection system based on a high-performance 15 MP (megapixel) sCMOS sensor and 4-quadrant spectral splitting.

Although commercial SMS sequencing systems have been available for five years, the rate of insertion and deletion errors remains above 10%. Although the error rate can be reduced in the case of Pacific BioSystems instruments by performing multiple reads on circular templates, the read length of these templates is limited to about 3 kb (4). A SMS system that incorporates real time error checking to reduce the rate of these errors would be a major advancement for the field of DNA sequencing. The challenge is to have a method to detect errors that integrates well with the required detection system to assess nucleotide incorporation.

EXAMPLES

The following examples are representative only.

Example 1

Prototype System to Detect Single Molecule Conformational Changes in DNA Polymerase I Klenow Fragment (KF) to Assess Insertion and Deletion Error Detection

1. Introduction.

Figure 1:
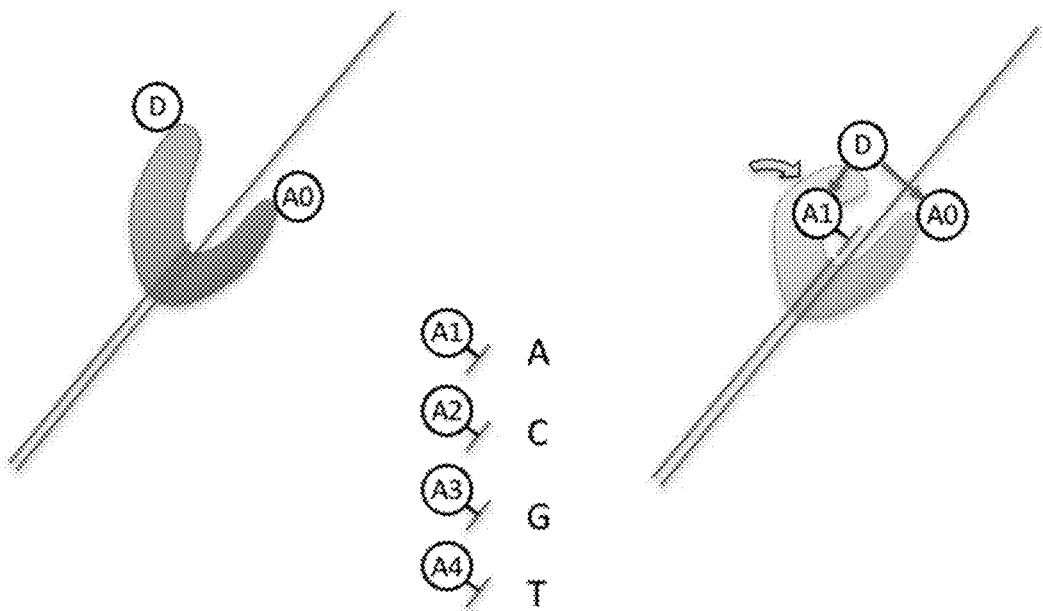
FIG. 1 illustrates the use of FRET to detect both the proximity of a labeled nucleotide analogue to the polymerase and the conformational change in the polymerase. In one example (FIG. 1, part A), a Donor moiety (D) is positioned on the "fingers" region of the polymerase, and an Acceptor moiety (A0) is positioned on the "thumb" region. Four other Acceptors (4 different dye complexes) in these embodiments are attached to the terminal phosphates on each of the nucleotide analogues (A1, A2, A3, and A4). The illustration on the left shows the polymerase (blue) in its "open" conformation bound to the template. On the right, the polymerase is shown in its "closed" conformation (green), with the A1-labeled-dNTP being incorporated into the daughter strand. When the complementary next nucleotide to be added to the primer extension product associates with the template strand in the polymerase's active site and the polymerase is in the "closed" position, there will be a FRET signal from both the A0 and A1 dyes. In some embodiments, the "Donors" and "Acceptors" are multi-dye complexes, to enhance the magnitude of the FRET signal.
Figure 1:
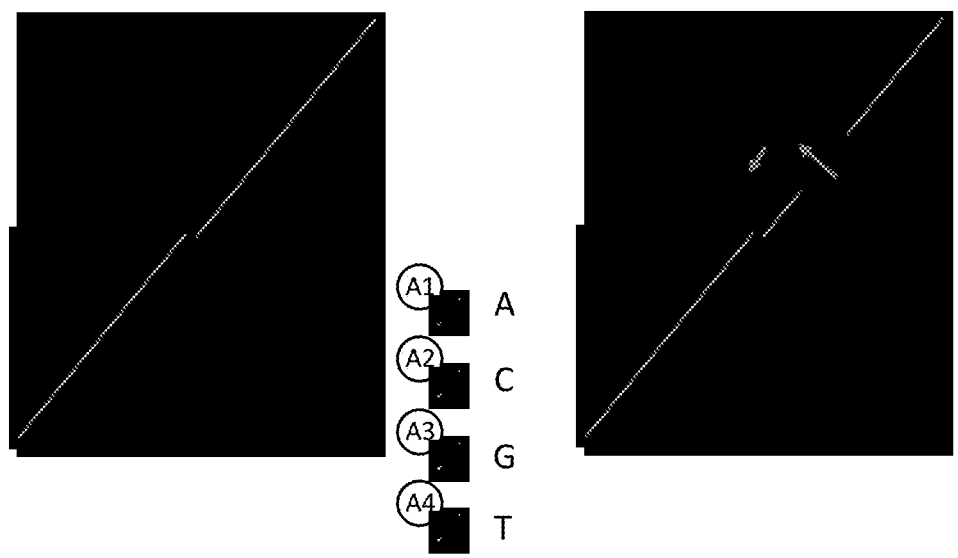

DNA polymerases are able to replicate DNA with very low error rates (e.g., 1 error per $10^5$ to $10^8$ correct nucleotide incorporations) and at speeds exceeding 500 nucleotide base incorporations per second (6). The high selectivity of replication exceeds the fidelity that would be expected based solely on free energy differences that would occur between correct versus incorrect base pairings (7). Therefore, DNA polymerases must be able to actively discriminate between correct and incorrect base pairing in addition to the proofreading function they possess that occurs after base incorporation. In addition, this kinetic "error-checking" process must also proceed rapidly to support required replication rates. The mechanics of this error checking is due to a series of noncovalent interactions between the incoming nucleotide and enzyme, which occur prior to the covalent phosphoryl transfer step of adding the nucleotide to the growing strand of replicating DNA ("elongation"). One step in this error check process is attributed to the conformational change of DNA polymerases where the moving parts of the enzyme are often described as a handlike structure with a "finger" region and "thumb" region (8). Several studies employing stopped flow kinetics have characterized the movement of these regions, which transition from an "open" to "closed" structure prior to the incorporation of a nucleotide base (9). The "open" conformation permits noncovalent binding of a deoxynucleotide triphosphate (dNTP) substrate to a DNA polymerase. Subsequently, this dNTP is then moved towards the enzyme active site by the movement of the finger region towards the thumb region, adopting a "closed" conformation (10). In this closed conformation, the triphosphate moiety of the dNTP is then aligned for reaction with the 3'-OH moiety of the replicating DNA strand, and the dNTP is then incorporated. An illustration of these conformational changes is shown in FIG. 1, along with the strategy for dye (i.e., energy transfer moiety) placement employed in the invention.

Representative energy donors and acceptors that can be used for FRET-based analyses in the context of the invention Alexa Fluor (AF) dyes. Table 1, below, shows several AF dye combinations.

TABLE 1

Alexa Fluor dyes.

| | Acceptor | | | | | |
|---|---|---|---|---|---|---|
| Donor | Alexa Fluor 488 | Alexa Fluor 546 | Alexa Fluor 555 | Alexa Fluor 568 | Alexa Fluor 594 | Alexa Fluor 647 |
| Alexa Fluor 350 | 50 | | | | | |
| Alexa Fluor 488 | NA | 64 | 70 | 62 | 60 | 56 |
| Alexa Fluor 546 | | NA | | 70 | 71 | 74 |
| Alexa Fluor 555 | | | NA | | 47 | 51 |
| Alexa Fluor 568 | | | | NA | | 82 |
| Alexa Fluor 594 | | | | | NA | 85 |
| Alexa Fluor 647 | | | | | | NA |

Table 1 shows R0 values for in Angstroms (Å) for several AF dyes. These R0 values represent the distance (in Å) at which fluorescence resonance energy transfer from the donor dye to the acceptor dye is 50% efficient (Förster radius).

2. Considerations for Insertion/Deletion Error Detection.

SMRT sequencing systems are typically hampered by insertion/deletion errors, in contrast to the shorter read sequencing by synthesis (SBS) systems where substitution errors play a greater role on platforms including the Illumina MiSeq (13). After obtaining results for the matched and mismatched nucleotides, there appears to be strong discrimination in smFRET behavior. In sequencing, major causes of errors are insertion and deletion errors (indel) or substitutions. An insertion error occurs when nucleotide incorporation is falsely called by the sequencer. By requiring observation of the more stable polymerase/DNA/dNTP signal to call a true incorporation, an insertion error can be flagged. Conversely, a deletion error occurs when a dNTP is incorporated but not flagged by the sequencer. By detecting the stable polymerase/DNA/dNTP signal via smFRET, this error can also be characterized. The smFRET signal can be monitored at a different wavelength from the signals used to identify the dNTP, providing an "orthogonal" error check system.

Example 2

DNA Polymerases

1. Polymerase Selection.

A key challenge encountered in the course of attempting long-range sequencing with a polymerase such as Phi29, is that the polymerase can become inactive and stop extending the daughter strand being synthesized from the template. This is likely caused by a photo-initiated mechanism, such as creation of free radicals in solution that damage the polymerase. Two approaches could be pursued to address this issue: 1) engineering a polymerase that is more robust to photo-induced damage; or 2) employing a different strategy for long extension—instead of using a very highly processive enzyme (long extension with a single enzyme molecule), using a more distributive enzyme which will be dynamically replaced with a fresh enzyme after it has gone through an average of about 20-100 base additions.

The first approach is possible, as evidenced by the success by companies, such as Pacific Biosciences, in developing a photo-robust polymerase capable of 10 Kb-20 Kb read lengths. The second approach, however, offers additional advantages, as the requirements placed on the polymerase in this approach are much more modest. Indeed, a similar approach is widely used in PCR reactions, where long stretches of DNA are copied by distributive enzymes that jump on/off every 50-100 bases (16). Fresh enzyme solution can, for example, be slowly flowed in during the course of sequencing run, at a rate sufficient to replace any photo-degraded polymerase.

Another advantage of the more distributive approach is that enzyme selection can be driven by other performance parameters, such as the desired speed (extension rate), fidelity, and ability to cleave large chemical groups. A preferred DNA polymerase is the Therminator Gamma polymerase (New England BioLabs). These polymerases have the ability to cleave the phosphate groups on dNTPs modified at the gamma phosphate position. They also have the desired moderate processivity of about 50 bases and an incorporation rate for unlabeled nucleotides on the order of 10-100 bases/sec; the rate is likely to be lower with the labeled nucleotides, and can be further slowed by specific modifications on the nucleotides, as was recently demonstrated (17).

2. Structure of Therminator Gamma Polymerases and Labeling Geometry.

Therminator Gamma DNA Polymerase is a genetically engineered form of the native DNA polymerase from *Thermococcus* species 9° N-7, and this structure has been published (18). The structure shows the thumb and finger domains that are a common motif across multiple polymerase families, and the structure furthermore alludes to a closing of the fingers relative to the thumb domain as part of the catalytic cycle of DNA polymerization (18). Furthermore, movement of the N-terminal domain relative to the catalytic domain of the palm region is supported, which may create further options for conformational monitoring in addition to labeling the thumb and finger domains.

Example 3

FRET Dyes

1. FRET Dye Complexes.

A challenge with single molecule sequencing is generating sufficient signal for robust detection. In one embodiment, using multiple donors increases the absorption cross-section, and hence the energy available for energy transfer to the acceptors via the Förster mechanism (19, 20). Multiply-labeled donors also have the advantage of being much more robust to photobleaching and blinking than a single dye molecule. As a further step to increase the readout signal and S/N ratio, multiply-labeled dye complexes are employed as the acceptors for the FRET process. Having multiple acceptors, rather than a single dye molecule, increases the energy transfer rate, and hence the magnitude and robustness of the FRET signal. It has been recently shown that nucleotides (dNTPs) can be labeled with very large complexes attached to the 5' position on the ribose ring (provided there is a hexaphosphate or larger linking moiety) and these complexes are effectively cleaved by polymerases (21). Oligomers as large as 100's of kD have been used as labels (for nanopore detection), attached via extended 5- or 6-phosphate linkages to the 5' position. A scaffold, such as Streptavidin, carrying 10 or more dyes, will be used as the acceptor moiety. The labeled SA will be coupled to a biotin that is attached via a poly-phosphate linkage to the nucleotide. An added benefit of this configuration is that different dyes can be quickly evaluated in optimizing the acceptor dye selection, since each of the 4 nucleotides will have a generic biotin linkage available. Biotin-labeled dNTPs that are polymerase-compatible and modified at the 5' position are commercially available as standard catalogue items from a number of sources, including VWR Scientific (Radnor, Pa.).

A multiply-labeled acceptor attached to the polymerase "fingers" as the indicator will also be used for conformational readout (see, e.g., FIG. 1) and labeled "Int" for intermediate acceptor. The polymerase labeling chemistry is performed employing a donor fluorophore ("D") on the thumb portion of the polymerase by introducing a cysteine moiety to allow coupling via maleimide chemistry as previously described (12). The cysteine is engineered into the polymerase by whole gene synthesis at the desired location. The intermediate acceptor at the finger position will again employ streptavidin attached to a biotin moiety, which can be attached to a specific residue containing an AviTag fusion sequence recognized by *E. coli* biotin ligase enzyme (22).

2. FRET Scheme for Detection of dNTPs and Conformational Monitoring.

A combination proximity detection of nucleotides is used with the conformational state monitoring of the polymerase. FIG. 1, part B, illustrates a representative cascading FRET approach. A donor ("D") will be positioned on the "thumb" region of the polymerase, and the Intermediate acceptor/donor on the fingers. The final acceptors ("A"; 4 different dye complexes) will be attached to the terminal phosphates on each of the nucleotides. When the nucleotides are bound to the template and the polymerase is in the closed position, there will be a cascading energy transfer process: from the optically excited donor (D), to the Intermediate ("Int"; acceptor/donor), and then on to the final acceptors (A1-A4).

The positioning of the donor (D) and intermediate (Int) labels will have a dual reinforcing effect in the generation of acceptor (A) signals in the closed conformation: the movement of the "finger" region will increase the FRET from donor (D) to intermediate (Int), and also increase the FRET from intermediate (Int) to acceptors (A's) on the nucleotides. Based on the previous studies, the overall cascade FRET efficiency is expected to increase approximately 2-3 fold compared to a nucleotide just transiently bound in the open state (5, 14).

3. FRET Fluorophore Selection.

For the identification of different nucleotides, the following 4 dyes can be used as acceptors: Dy634, AF647, AF676, and AF700. These dyes have been proven to yield enough spectral separation to provide accurate base calling. These dyes will be excited by an AF555 dye at the Int position as shown in FIG. 1, part B. For conformational monitoring, an AF488 donor dye at the thumb position will initially be employed. Due to the possibility of excitation of AF555 by the laser employed to excite AF488, a transition to a lower wavelength conformational donor dye may be required, for example, CF440 or CF450, in which event a different light source may be required.

TABLE 2 signals for each of the dyes in different states (only the A1 labeled dNTP is shown, but the A2, A3, and A4 dNTPs would produce corresponding signals)

|  | Donor | Intermediate | A1 | A2 | A3 | A4 |
|---|---|---|---|---|---|---|
| No polymerase bound | 0 | 0 | 0 | 0 | 0 | 0 |
| Open, no dNTP | +++ | + | 0 | 0 | 0 | 0 |
| Closed, no dNTP | + | +++ | 0 | 0 | 0 | 0 |
| Open, dNTP-A1 present | +++ | + | + | 0 | 0 | 0 |
| Closed, dNTP-A1 bound | + | ++ | +++ | 0 | 0 | 0 |
| Etc. | | | | | | |

Thus, the relative signal intensities will differentiate between a dNTP that is transiently present in the binding region versus a dNTP that is bound with the polymerase in its closed state. In addition to the difference in signal intensities, the temporal signature of a true binding and incorporation events will be quite different from transient binding, as seen in past work (5) and the research described above.

A practical challenge in this approach is the need to simultaneously measure the fluorescence intensity from 6 dyes—donor (D), intermediate (Int), and acceptors (A1, A2, A3, and A4). This is accomplished by using four spectral channels. Two of the spectral channels are dedicated to the donor (D) and intermediate (Int), which are spectrally well separated. Two additional spectral channels will be used to measure the signals from A1, A2, A3, and A4. Since at any given time only one of these labeled dNTPs will be in the FRET detection zone, they can be uniquely identified by a linear combination of the two spectral channels, as shown in FIG. 2.

Example 4

TIRF/FRET Optical System

The results presented above demonstrate the feasibility of detecting nucleotide binding and polymerase conformational change via FRET driven by total internal reflection fluorescence (TIRF). TIRF provides the confinement of the excitation volume to the evanescent field that extends 100-150 nm beyond the glass substrate surface. This minimizes background fluorescence outside of that narrow volume, and provides the low background measurements necessary to detect single molecule fluorescence. The results presented above used 2 different TIRF illumination modalities: prism-based TIRF (p-TIRF) and through-the-objective TIRF (o-TIRF). These are illustrated in FIG. 3, along with a third modality, grating-based TIRF (g-TIRF).

Objective TIRF uses a high NA objective and index-matching oil to deliver light at above the critical angle for total internal reflection at the glass/water interface. While o-TIRF offers a convenient approach for research studies, it has a number of practical limitations: the required 100× objectives with NA>1.4 have a very small field of view (e.g., 100 um for a 10 mm detector), which limits the number of templates that can be monitored and hence the sequencing throughput. Also, o-TIRF has more background auto-fluorescence, because the excitation light is directed through the objective.

The prism-coupled TIRF illumination of p-TIRF completely separates the illumination light path from the fluorescence emission light path, thereby achieving the lowest auto-fluorescence background. Additionally, since the laser beam is directly delivered to the substrate, the illumination efficiency can be significantly greater than o-TIRF, which allows for the use of a less powerful and less expensive laser source.

Grating-coupled TIRF illumination has the additional advantage of not requiring a prism to be part of the flow cell. Rather, the laser light can be coupled in via a grating fabricated directly on the glass cover slip. Grating-coupled TIRF also offers the possibility to couple the illumination into a thin waveguide with a high index of refraction, such as $Ta_2O_5$ (n=2.12). The higher index of refraction produces an even shorter evanescent field (~20-30 nm), further suppressing any unwanted background fluorescence generated in solution.

Both prism-TIRF and grating-TIRF allow for a wider selection of imaging objectives, since they do not require an oil-coupled low-fluorescence objective with NA>1.4. There is a considerable practical advantage in using an air-coupled objective (which eliminates the need for index-matching oil). An air-coupled objective is limited to a maximum NA of 1.0, if all the light is captured, and in practice, limited to 0.95. An example of this type of objective is the 40×, 0.95 NA version (Nikon, CFI Plan Apo Lambda 40×). There is a further advantage in being able to use an objective with a slightly lower NA, as this relieves highly demanding constraints in the optical design, and allows the design of a lower-magnification objective. The larger field of view results in an increase in the number of DNA templates that can be observed simultaneously and hence higher throughput can be achieved. For example, a 40× objective has a 6.25× greater field of view compared to a 100× objective, while the resolution difference is modest given the small decrease in NA. Considering the resolution and field of view, the effective amount of information that be imaged through the 40×, 0.95 NA objective is about 12 million pixels.

With higher FRET signal levels provided by multiply-labeled donors and acceptors, the system will have the flexibility to use such an air-coupled objective with a large field of view for high throughput.

Example 5

Detection System

1. Imaging Detector for Single-Molecule Fluorescence.

With increased FRET signal intensity, robust polymerase conformational monitoring, and extended read lengths, the throughput of the detection system can be increased. High throughput can be accomplished using a detection sensor with a very large number of pixels, extremely fast readout speed, low electronic noise, and high quantum efficiency. Sensors meeting these requirements are available, based on the latest developments in sCMOS technology. Over the last decade, single-molecule imaging measurements have predominantly used electron-multiplication CCDs (EMCCD), which had replaced intensified CCDs (ICCDs) used previously. While EMCCDs were a significant advance over ICCDS in terms of signal stability and relatively lower cost, they still have limitations in readout speed, number of pixels, and considerable cost. In the last few years, the electronics of sCMOS-based cameras have improved greatly, such that the latest cameras have an electronic noise of about 1 e/pixel, and are becoming competitive with EMCCDs. The most advanced sCMOS camera currently available, Prime 95B, launched in November 2016 by Photometrics, has a peak quantum efficiency of 95% (photon to electron conversion), and a read noise of 1 e/pixel. This camera has a 4MP sensor (2K×2K) and a frame rate of up to 100 frames/sec. Such high frame rates are achievable in such a large pixel format because the readout of pixels on a sCMOS sensor occurs in parallel on independent A/D circuits on each pixel, rather than the serial readout through a single A/D used in CCDs. Cameras with an even larger array of pixels are in development, which will further extend the capabilities of sCMOS-based cameras. The table below compares the key performance metrics for a typical EMCCD and three versions of sCMOS-based cameras. It should be noted that sCMOS cameras are also less expensive that EMCCD cameras, roughly by 30-50%. A comparison of options is given below in Table 3, below.

TABLE 3 a comparison of performance parameters for recent sCMOS and EMCCD camera options.

| Camera | Technology | Pixels | QE | Noise | Full frame rate | Pixel readout rate |
|---|---|---|---|---|---|---|
| | EMCCD | 0.25 MP (512 × 512) | | <1 e/pixel | 30 fps | 7 MP/sec |
| Prime | sCMOS | 1.2 MP (1100 × 1100) | 65% | 1 e/pixel | 100 fps | 120 MP/sec |
| Prime 95B | sCMOS | 4 MP (2K × 2K) | 95% | 1 e/pixel | 100 fps | 400 MP/sec |
| In development | sCMOS | 15 MP (5K × 3K) | TBD | 1 e/pixel | 100 fps (target) | 1500 MP/sec |

Combined with an objective with sufficiently high space-bandwidth product (SBP), the latest sCMOS camera technology offers an unprecedented pixel readout rate, ideal for high-throughput, high-speed sequencing.

For a commercially viable sequencing system, the cost of the instrument is an important factor. In a real-time optical detection system, the high-performance cameras make up a significant portion of the costs. With this in mind, some preferred systems use a single large-format sCMOS camera rather than multiple EMCCD cameras. The multiple spectral channels of the fluorescence emission will be split into 4 quadrants on the single camera, as shown below. With a 15 MP camera, there will be more than 3 MP available in each quadrant, which is sufficient for a very high throughput system. In addition to the cost benefits of using a single sensor rather than several, there is also the advantage of automatic synchronization of the readout on all the spectral channels. An example of a commercially available four-channel beam splitter is the Photometrics QV2, which can be adapted for use in accordance with the current invention.

2. System Throughput.

A critical performance metric of any DNA sequencing system is the throughput, or the number of bases that can be sequenced in a single run. In this invention, the advantages of long reads can be combined with high-throughput. As described above, 3M pixels are available to image the DNA templates in each of the 4 colors, and more than adequate resolution and field of view in the microscope. The number of pixels on average needed to be allocated to each template will be in the range 5-10 pixels/template. At 10 pixels/template, up to 300,000 sequencing reactions can be simultaneously observed. At a sequencing rate of 10 bases/sec, the output will be 3 Mb/sec, or 10 Gb/hour, far exceeding current long-read techniques and competitive even with the leading short-read high-throughput sequencer, Illumina's HiSeqX, which produces 1.8 Tb in a 3 day run, or ~10 Gb/hr.

3. Maintaining Surface Proximity for Long Reads.

As the complementary strand is extended, the position of the polymerase complex can be more distant from the surface. TIRF coupling limits the optical excitation range to within approximately 100-150 nm of the glass surface. DNA base spacing is approximately 0.3 nm, and the dsDNA takes on a non-straight configuration, so for the sequencing position will remain with the TIRF range for at least ~1000 bases. However, to get much longer read lengths, a "capturing" approach will be used to "tether" the nascent dsDNA product to the surface. In some such preferred embodiments, the substrate surface will be sparsely coated with antibodies that bind dsDNA. See, e.g., FIG. 5. As the complementary strand is formed, it will periodically form additional attachment points to the surface, mediated by binding of antibodies to the dsDNA portions of the parent:daughter strand complex.

As will be appreciated, in addition to antibody-based methods for tethering dsDNA, any other suitable approach to tether the nascent dsDNA product to the surface of the solid substrate can also be used. For example, the DNA template can be immobilized on or to the solid substrate, e.g., by covalent linkage to the template's 3' end; by attaching a polynucleotide linker or adapter to the template's 3' terminus, which can then hybridize a complementary polynucleotide laid down on the surface of the solid substrate, which linker or adapter could also include, for example, a primer binding site. Alternatively, compounds such as intercalating agents, sequence-specific polyamides, DNA binding proteins, and associated with the surface of the solid substrate can also be used to tether the nascent dsDNA product to the substrate.

Tethering will maintain the required proximity to the surface for TIRF excitation. It will also have the added advantage of providing a robust secondary attachment mechanism for long double-stranded products, limiting the possibility of the template being detached during the sequencing run.

4. Image Processing and Data Analysis.

The images collected in each of the 4 channels are aligned with subpixel resolution, and individual template-bound polymerases are tracked in time. Matched filtering is applied to optimally extract signal from noise. Homopolymer sequences in synthetic templates will be used to determine the specific spectral and temporal signatures of base incorporation events. The characteristics of various sources of background noise (electronic and optical) will also be characterized so they can be optimally digitally filtered out. With robust base calling signatures in hand, sequencing accuracy will be analyzed using defined pseudo-random templates. Initially, experiments will be done at low template density to simplify the template tracking; the maximum density that can be achieved without compromising accuracy will then be experimentally and computationally determined.

REFERENCES CITED IN SPECIFICATION

1. Gupta P K. Single-molecule DNA sequencing technologies for future genomics research. Trends Biotechnol. 2008; 26(11):602-11. doi: 10.1016/j.tibtech.2008.07.003. PubMed PMID: 18722683.
2. Ossola A. Your Full Genome Can Be Sequenced for Just $1000. Popular Science. 2015.
3. Miller N A, Farrow E G, Gibson M, Willig L K, Twist G, Yoo B, Marrs T, Corder S, Krivohlavek L, Walter A, Petrikin J E, Saunders C J, Thiffault I, Soden S E, Smith L D, Dinwiddie D L, Herd S, Cakici J A, Catreux S, Ruehle M, Kingsmore S F. A 26-hour system of highly sensitive whole genome sequencing for emergency management of genetic diseases. Genome Med. 2015; 7:100.

doi: 10.1186/s13073-015-0221-8. PubMed PMID: 26419432; PMCID: PMC4588251.
4. Eid J, Fehr A, Gray J, Luong K, Lyle J, Otto G, Peluso P, Rank D, Baybayan P, Bettman B, Bibillo A, Bjornson K, Chaudhuri B, Christians F, Cicero R, Clark S, Dalal R, Dewinter A, Dixon J, Foquet M, Gaertner A, Hardenbol P, Heiner C, Hester K, Holden D, Kearns G, Kong X, Kuse R, Lacroix Y, Lin S, Lundquist P, Ma C, Marks P, Maxham M, Murphy D, Park I, Pham T, Phillips M, Roy J, Sebra R, Shen G, Sorenson J, Tomaney A, Travers K, Trulson M, Vieceli J, Wegener J, Wu D, Yang A, Zaccarin D, Zhao P, Zhong F, Korlach J, Turner S. Real-time DNA sequencing from single polymerase molecules. Science. 2009; 323(5910):133-8. doi: 10.1126/science.1162986. PubMed PMID: 19023044.
5. Berezhna S Y, Gill J P, Lamichhane R, Millar D P. Single-molecule Förster resonance energy transfer reveals an innate fidelity checkpoint in DNA polymerase I. Journal of the American Chemical Society. 2012; 134(27): 11261-8. doi: 10.1021/ja3038273. PubMed PMID: 22650319; PMCID: PMC3448555.
6. Pomerantz R T, O'Donnell M. Replisome mechanics: insights into a twin DNA polymerase machine. Trends Microbiol. 2007; 15(4):156-64. doi: 10.1016/j.tim.2007.02.007. PubMed PMID: 17350265.
7. Kunkel T A. DNA replication fidelity. The Journal of biological chemistry. 2004; 279(17):16895-8. doi: 10.1074/jbc.R400006200. PubMed PMID: 14988392.
8. Li Y, Korolev S, Waksman G. Crystal structures of open and closed forms of binary and ternary complexes of the large fragment of *Thermus aquaticus* DNA polymerase I: structural basis for nucleotide incorporation. The EMBO journal. 1998; 17(24):7514-25. doi: 10.1093/emboj/17.24.7514. PubMed PMID: 9857206; PMCID: PMC1171095.
9. Joyce C M, Potapova O, Delucia A M, Huang X, Basu V P, Grindley N D. Fingers-closing and other rapid conformational changes in DNA polymerase I (Klenow fragment) and their role in nucleotide selectivity. Biochemistry. 2008; 47(23):6103-16. doi: 10.1021/bi7021848. PubMed PMID: 18473481.
10. Stengel G, Gill J P, Sandin P, Wilhelmsson L M, Albinsson B, Norden B, Millar D. Conformational dynamics of DNA polymerase probed with a novel fluorescent DNA base analogue. Biochemistry. 2007; 46(43): 12289-97. doi: 10.1021/bi700755m. PubMed PMID: 17915941.
11. Lakowicz J R. Principles of frequency-domain fluorescence spectroscopy and applications to cell membranes. Subcell Biochem. 1988; 13:89-126. PubMed PMID: 2577864.
12. Santoso Y, Joyce C M, Potapova O, Le Reste L, Hohlbein J, Torella J P, Grindley N D, Kapanidis A N. Conformational transitions in DNA polymerase I revealed by single-molecule FRET. Proceedings of the National Academy of Sciences of the United States of America. 2010; 107(2):715-20. doi: 10.1073/pnas.0910909107. PubMed PMID: 20080740; PMCID: PMC2818957.
13. Schirmer M, Ijaz U Z, D'Amore R, Hall N, Sloan W T, Quince C. Insight into biases and sequencing errors for amplicon sequencing with the Illumina MiSeq platform. Nucleic Acids Res. 2015; 43(6):e37. doi: 10.1093/nar/gku1341. PubMed PMID: 25586220; PMCID: PMC4381044.
14. Evans G W, Hohlbein J, Craggs T, Aigrain L, Kapanidis A N. Real-time single-molecule studies of the motions of DNA polymerase fingers illuminate DNA synthesis mechanisms. Nucleic Acids Res. 2015; 43(12):5998-6008. doi: 10.1093/nar/gkv547. PubMed PMID: 26013816; PMCID: PMC4499156.
15. Schneckenburger H. Total internal reflection fluorescence microscopy: technical innovations and novel applications. Curr Opin Biotechnol. 2005; 16(1):13-8. doi: 10.1016/j.copbio.2004.12.004. PubMed PMID: 15722010.
16. Osheroff W P, Jung H K, Beard W A, Wilson S H, Kunkel T A. The fidelity of DNA polymerase beta during distributive and processive DNA synthesis. The Journal of biological chemistry. 1999; 274(6):3642-50. PubMed PMID: 9920913.
17. He M, Chen C Y, Kool E, Ronaghi M, Previte M, Pantoja R, inventors; Illumina, assignee. Conformational Probes and Methods for Sequencing Nucleic Acids. USA 2016.
18. Rodriguez A C, Park H W, Mao C, Beese L S. Crystal structure of a pol alpha family DNA polymerase from the hyperthermophilic archaeon *Thermococcus* sp. 9 degrees N-7. Journal of molecular biology. 2000; 299(2):447-62. doi: 10.1006/jmbi.2000.3728. PubMed PMID: 10860752.
19. Corry B, Jayatilaka D, Rigby P. A Flexible Approach to the Calculation of Resonance Energy Transfer Efficiency between Multiple Donors and Acceptors in Complex Geometries. Biophysical Journal. 2005; 89:3822-36.
20. Maliwal B P, Raut S, Fudala R, D'Auria S, Marzullo V M, Luini A, Gryczynski I, Gryczynski Z. Extending Förster resonance energy transfer measurements beyond 100 Å using common organic fluorophores: enhanced transfer in the presence of multiple acceptors. J Biomed Opt. 2012; 17(1):011006. doi: 10.1117/1.JBO.17.1.011006. PubMed PMID: 22352640; PMCID: PMC3379572.
21. Fuller C W, Kumar S, Porel M, Chien M, Bibillo A, Stranges P B, Dorwart M, Tao C, Li Z, Guo W, Shi S, Korenblum D, Trans A, Aguirre A, Liu E, Harada E T, Pollard J, Bhat A, Cech C, Yang A, Arnold C, Palla M, Hovis J, Chen R, Morozova I, Kalachikov S, Russo J J, Kasianowicz J J, Davis R, Roever S, Church G M, Ju J. Real-time single-molecule electronic DNA sequencing by synthesis using polymer-tagged nucleotides on a nanopore array. Proceedings of the National Academy of Sciences of the United States of America. 2016; 113(19): 5233-8. doi: 10.1073/pnas.1601782113. PubMed PMID: 27091962; PMCID: PMC4868432.
22. Fairhead M, Howarth M. Site-specific biotinylation of purified proteins using BirA. Methods in molecular biology. 2015; 1266:171-84. doi: 10.1007/978-1-4939-2272-7_12. PubMed PMID: 25560075; PMCID: PMC4304673.

All of the devices, systems, and methods disclosed and claimed herein can be made and executed without undue experimentation in light of the present disclosure. While the devices, systems, and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. It will also be appreciated that computer-based embodiments of the instant invention can be implemented using any suitable hardware and software.

All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of single-molecule, real-time nucleic acid sequencing-by-synthesis, comprising:
    a. performing on a solid substrate a plurality of single-molecule, real-time nucleic acid molecule sequencing-by-synthesis reactions using a plurality of independently resolvable polymerase-template complexes,
       wherein each independently resolvable polymerase-template complex comprises a polymerase enzyme and a nucleic acid template, which nucleic acid template comprises a priming region complementary to a primer that can be extended by addition of one or more nucleotides by the polymerase enzyme to form an extension product,
       wherein the polymerase enzyme has been modified to allow (i) proximity sensing of at least one labeled nucleotide analogue species when a molecule of the labeled nucleotide analogue species associates with the polymerase enzyme proximate to the nucleic acid template; and (ii) sensing of a conformational change in the polymerase enzyme upon polymerase-mediated addition of a labeled nucleotide analogue to the primer or extension product,
       wherein sensing the conformation change comprises a first FRET from a first energy donor moiety attached to the polymerase enzyme at a first position to an intermediate energy acceptor/donor moiety attached to the polymerase enzyme at a second position when a conformational change in the polymerase enzyme occurs upon polymerase-mediated addition of a nucleotide to the primer or extension product, and
       wherein the proximity sensing comprises a second FRET from the intermediate energy acceptor/donor moiety to a second energy acceptor moiety of a labeled nucleotide analogue species when a molecule of the labeled nucleotide analogue species associates with the polymerase enzyme proximate to the nucleic acid template in a position associated with extension, which second FRET results in fluorescence indicative of the identity of the labeled nucleotide analogue species incorporated into the extension product;
    b. exposing the solid substrate and polymerase-template complexes to a sequencing reaction mixture comprising primers and a plurality of nucleotide analogue species, each of which is a different labeled nucleotide analogue species, wherein each of the different labeled nucleotide analogue species comprises a second energy acceptor moiety having a fluorescence spectrum that resolvably differs from the fluorescence spectra of the other labeled nucleotide analogue species;
    c. allowing sequencing reactions by the polymerase-template complexes, primers, and nucleotide analogue species to proceed;
    d. detecting fluorescence events from the sequencing reactions; and
    e. for a given independently resolvable polymerase-template complex, calling a nucleotide addition corresponding to the labeled nucleotide analogue species when, at substantially the same time, (i) proximate association of the labeled nucleotide analogue species and polymerase enzyme and (ii) and a conformational change in the polymerase enzyme, is sensed.

2. A method of single-molecule, real-time nucleic acid sequencing-by-synthesis, comprising:
    a. performing on a solid substrate a plurality of single-molecule, real-time nucleic acid molecule sequencing-by-synthesis reactions using a plurality of independently resolvable polymerase-template complexes,
       wherein each independently resolvable polymerase-template complex comprises a polymerase enzyme and a nucleic acid template, which nucleic acid template comprises a priming region complementary to a primer that can be extended by addition of one or more nucleotides by the polymerase enzyme to form an extension product,
       wherein the polymerase enzyme has been modified to allow (i) proximity sensing of at least one labeled nucleotide analogue species when a molecule of the labeled nucleotide analogue species associates with the polymerase enzyme proximate to the nucleic acid template; and (ii) sensing of a conformational change in the polymerase enzyme upon polymerase-mediated addition of a labeled nucleotide analogue to the primer or extension product,
       wherein sensing the conformational change comprises a first FRET from an energy donor moiety attached at a first position of the polymerase enzyme to a first energy acceptor moiety attached to the polymerase at a second position when a conformational change in the polymerase enzyme occurs upon polymerase-mediated addition of a labeled nucleotide analogue to the primer or extension product, which first FRET results in fluorescence indicative of the conformational change in the polymerase enzyme that occurs when a nucleotide analogue species is incorporated into the extension product, and
       wherein the proximity sensing comprises a second FRET from the energy donor moiety to a second energy acceptor moiety of a labeled nucleotide analogue species when a molecule of the labeled nucleotide analogue species associates with the polymerase enzyme proximate to the nucleic acid template in a position associated with extension, which second FRET results in fluorescence indicative of the identity of the labeled nucleotide analogue species incorporated into the extension product;
    b. exposing the solid substrate and polymerase-template complexes to a sequencing reaction mixture comprising primers and a plurality of nucleotide analogue species, each of which is a different labeled nucleotide analogue species, wherein each of the different labeled nucleotide analogue species comprises a second energy acceptor moiety having a fluorescence spectrum that resolvably differs from the fluorescence spectra of the other labeled nucleotide analogue species;

c. allowing sequencing reactions by the polymerase-template complexes, primers, and nucleotide analogue species to proceed;

d. detecting fluorescence events from the sequencing reactions; and e. for a given independently resolvable polymerase-template complex, calling a nucleotide addition corresponding to the labeled nucleotide analogue species when, at substantially the same time, (i) proximate association of the labeled nucleotide analogue species and polymerase enzyme and (ii) and a conformational change in the polymerase enzyme, is sensed.

3. A method according to claim 1, wherein the sequencing-by-synthesis reactions comprise four different nucleotide analogue species, some or all of which are differentially labeled such that each labeled nucleotide analogue species can be distinguished from the other labeled nucleotide analogue species.

4. A method according to claim 1, wherein addition of nucleotide analogue residues to primers or extension products is detected using fluorescence or electronically.

5. A method according to claim 1, wherein addition of nucleotide analogue residues to primers or extension products is detected by electrochemistry, capacitance, conductivity, impedance, or with a field effect transducer.

6. A method according to claim 1, wherein addition of nucleotide analogue residues to primers or extension products is detected by Förster resonance energy transfer (FRET) or total internal reflectance fluorescence (TIRF) or using a zero-mode waveguide or a plasmonic antenna.

7. A method according to claim 1, wherein (i) a 3' region of the nucleic acid template is attached directly or indirectly to the solid substrate, or (ii) an oligonucleotide complementary to a sequence of nucleotides in the nucleic acid template is attached directly or indirectly to the solid substrate.

8. A method according to claim 7, wherein at least one extension product binds to at least one proximate secondary DNA binding site on the substrate.

9. A method according to claim 8, wherein binding of the extension product at the proximate secondary DNA binding site is mediated by a DNA anchoring agent attached to the substrate, wherein the DNA anchoring agent optionally is a dsDNA binding antibody or antigen binding fragment thereof, a DNA binding protein or DNA-binding fragment thereof, or a small molecule that binds dsDNA.

10. A method according to claim 1, wherein the polymerase enzyme is attached to or immobilized on the substrate.

* * * * *